(12) United States Patent
Lu (10) Patent No.: US 8,721,729 B1
(45) Date of Patent: May 13, 2014

(54) CONNECTING DEVICE OF JOINT PROSTHESIS

(71) Applicant: United Orthopedic Corporation, Hsinchu (TW)

(72) Inventor: Cheng-Kuang Lu, Hsinchu (TW)

(*) Notice: Subject to any disclaimer, the term of this patent is extended or adjusted under 35 U.S.C. 154(b) by 0 days.

(21) Appl. No.: 13/746,140

(22) Filed: Jan. 21, 2013

(30) Foreign Application Priority Data

Dec. 17, 2012 (TW) ............................. 101224439 A (51) Int. Cl.
*A61F 2/38* (2006.01)
(52) U.S. Cl.
USPC ................... 623/20.15; 623/20.34; 623/23.44
(58) Field of Classification Search
USPC ........... 623/20.15, 20.34, 23.35, 23.44, 23.47
See application file for complete search history.

(56) References Cited

U.S. PATENT DOCUMENTS

| | | | | |
|---|---|---|---|---|
| 5,326,359 A | * | 7/1994 | Oudard | 623/20.36 |
| 6,953,479 B2 | * | 10/2005 | Carson et al. | 623/20.15 |
| 8,540,775 B2 | * | 9/2013 | Reich et al. | 623/20.15 |

* cited by examiner

*Primary Examiner* — Bruce E Snow
(74) *Attorney, Agent, or Firm* — Thomas Horstemeyer, LLP (57) ABSTRACT

A connecting device of joint prosthesis includes a stem means provided for being inserted into a medullary cavity of a bone, a receiving means provided for receiving a bone structure near the bone, an offset connecting means connected between the stem means and the receiving means, and an inserting member. The offset connecting means includes a first connecting component and a second connecting component. The inserting member inserts into an inserting bore of the first connecting component and an inserting recess of the second connecting component to make the first connecting component being fixed and positioned at the second connecting component, wherein there is an offset distance between the longitudinal central axis of the first connecting component and the longitudinal central axis of the second connecting component. Thereby the connecting device of joint prosthesis is adjustable for fitting individual patients with more effect in regard of the musculoskeletal mechanics.

8 Claims, 10 Drawing Sheets

CONNECTING DEVICE OF JOINT PROSTHESIS

CROSS-REFERENCE TO RELATED APPLICATION

This application claims priority to, and the benefit of, Taiwanese Patent Application entitled, "CONNECTING DEVICE OF JOINT PROSTHESIS," having application number 101224439, filed on Dec. 17, 2012, which is incorporated by reference in its entirety.

FIELD OF THE INVENTION

The present invention relates to a connecting device of joint prosthesis, and more particularly to a connecting device of joint prosthesis that is adjustable for shifting its longitudinal central axis.

BACKGROUND OF THE INVENTION

Joint prosthesis is an artificial implant. Some human joint problems, such as proliferation of bone spurs and articular surface degeneration, caused by unexpected accidents, sport injuries, repetitive pressures, or pathological changes may need to replace the human joint with the joint prosthesis by means of surgical operations. There are various joint prostheses, such as artificial knee, artificial hip, artificial shoulder, and artificial wrist.

The joint prosthesis generally includes a connecting device which is implanted into a medullary cavity of a bone and is for receiving a bone structure near the bone. However, the bone and the muscle are structurally different for every individual person, so the connecting device of the joint prosthesis should be designed for individual patients regarding musculoskeletal mechanics so as to be suitable for patients and to help patients recover.

SUMMARY OF THE INVENTION

However, the specification of conventional connecting device of joint prosthesis is designed regardless of musculoskeletal mechanics and biological diversity, and thus it is not easy to match human body for most of patients. The unmatched implanted joint prosthesis may be easily broken and cause some problems such as activity limitations, muscle stiffness, muscle pain, and even re-replacement surgery for patients.

Accordingly, an aspect of the present invention is to provide a connecting device of joint prosthesis which is adjustable for matching.

The connecting device of joint prosthesis comprises a stem means, a receiving means, an offset connecting means, and an inserting member. The stem means is provided for being inserted into a medullary cavity of a bone. The receiving means is provided for receiving a bone structure near the bone. The offset connecting means is connected between the stem means and the receiving means. The offset connecting means includes a first connecting component and a second connecting component. The first connecting component has an inserting bore. The second connecting component has an inserting recess. The inserting member inserts into the inserting bore and the inserting recess to make the first connecting component being fixed and positioned at the second connecting component, wherein there is an offset distance between the longitudinal central axis of the first connecting component and the longitudinal central axis of the second connecting component.

According to an embodiment of the present invention, the inserting member is a screw member or a pin.

According to an embodiment of the present invention, the first connecting component connects with the stem means or with the receiving means by means of a column body.

According to an embodiment of the present invention, the inserting bore penetrates the column body.

According to an embodiment of the present invention, the inserting recess has an inner screw section, the inserting member passes into the inserting bore and is fixed by the inner screw section.

According to an embodiment of the present invention, the second connecting component has a plurality of the inserting recesses.

According to an embodiment of the present invention, the second connecting component has two convex bodies formed on an end facing the first connecting component thereof, the inserting recess locates between the two convex bodies, and the inserting member inserts into the inserting recess in a direction orthogonal to a depth direction of the inserting recess.

According to an embodiment of the present invention, the first connecting component has an engaging groove for an engaging bump of the second connecting component sliding into.

According to an embodiment of the present invention, the inserting bore is formed on a sidewall of the first connecting component.

According to an embodiment of the present invention, the longitudinal central axis of the first connecting component and the longitudinal central axis of the second connecting component are skew to each other.

By means of technical means of the present invention, the connecting device of joint prosthesis is adjustable so that its longitudinal central axis can be shifted. Thereby the joint prosthesis can be matching in view of the musculoskeletal mechanics. So the musculoskeletal stability and the musculoskeletal activity can be maintained, and also the stress concentration and the joint wear can be prevented from. It helps patients recover to return to normal activities. Moreover, the connecting device of joint prosthesis of the present invention is easy and convenient to be assembled and adjusted.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

The First Embodiment

Figure 1:
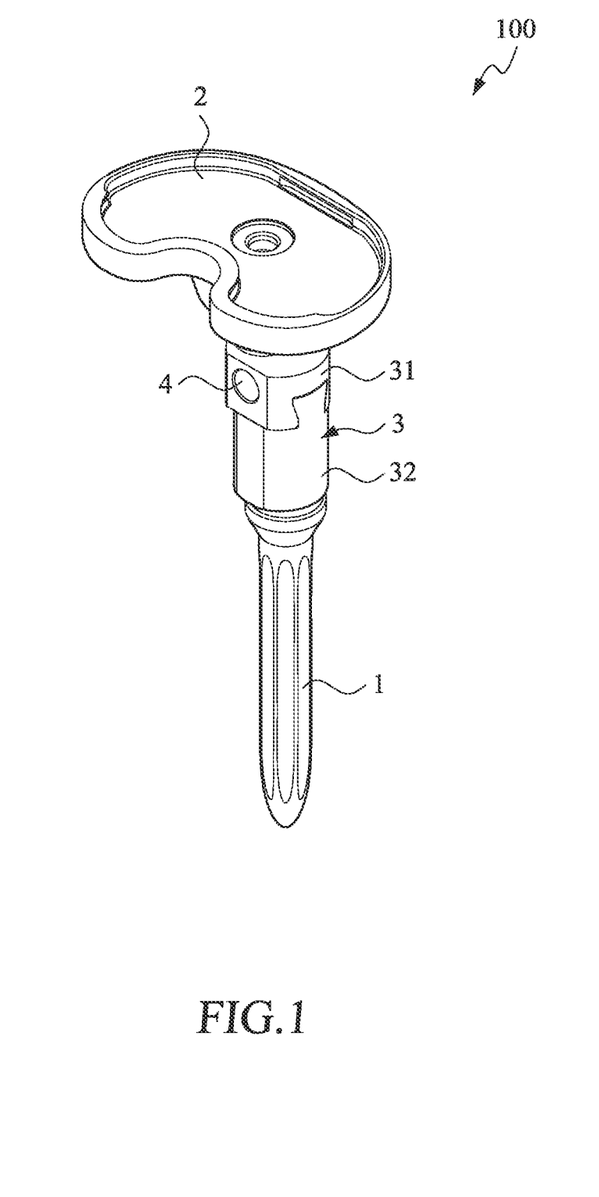
FIG. 1 is a stereogram illustrating the connecting device of joint prosthesis of the first embodiment according to the present invention.
Figure 2:
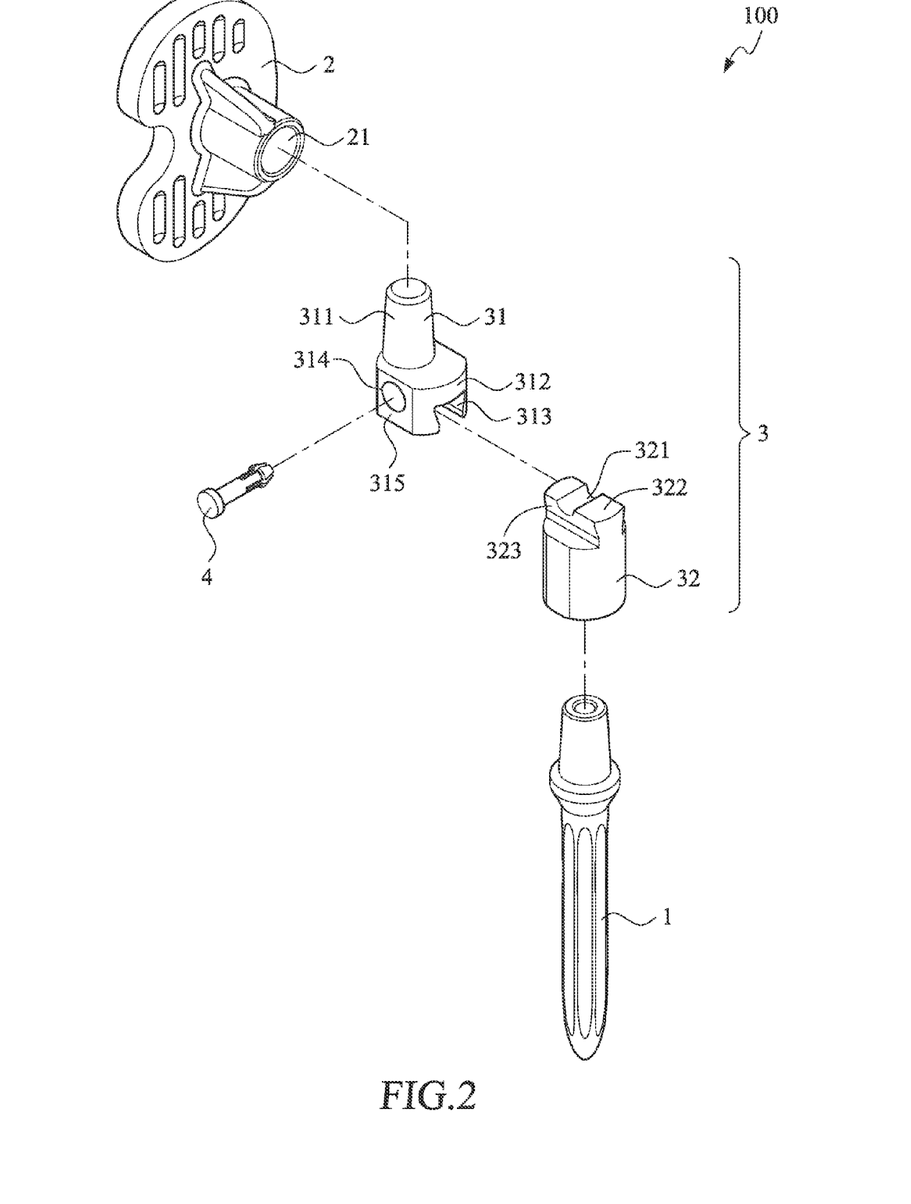
FIG. 2 is an explosion diagram illustrating the connecting device of joint prosthesis of the first embodiment according to the present invention.

Refer to FIG. 1 and FIG. 2. FIG. 1 is a stereogram illustrating the connecting device of joint prosthesis of the first embodiment according to the present invention. FIG. 2 is an explosion diagram illustrating the connecting device of joint prosthesis of the first embodiment according to the present invention. The connecting device of joint prosthesis 100 of the first embodiment according to the present invention comprises a stem means 1, a receiving means 2, an offset connecting means 3, and an inserting member 4.

Figure 3:
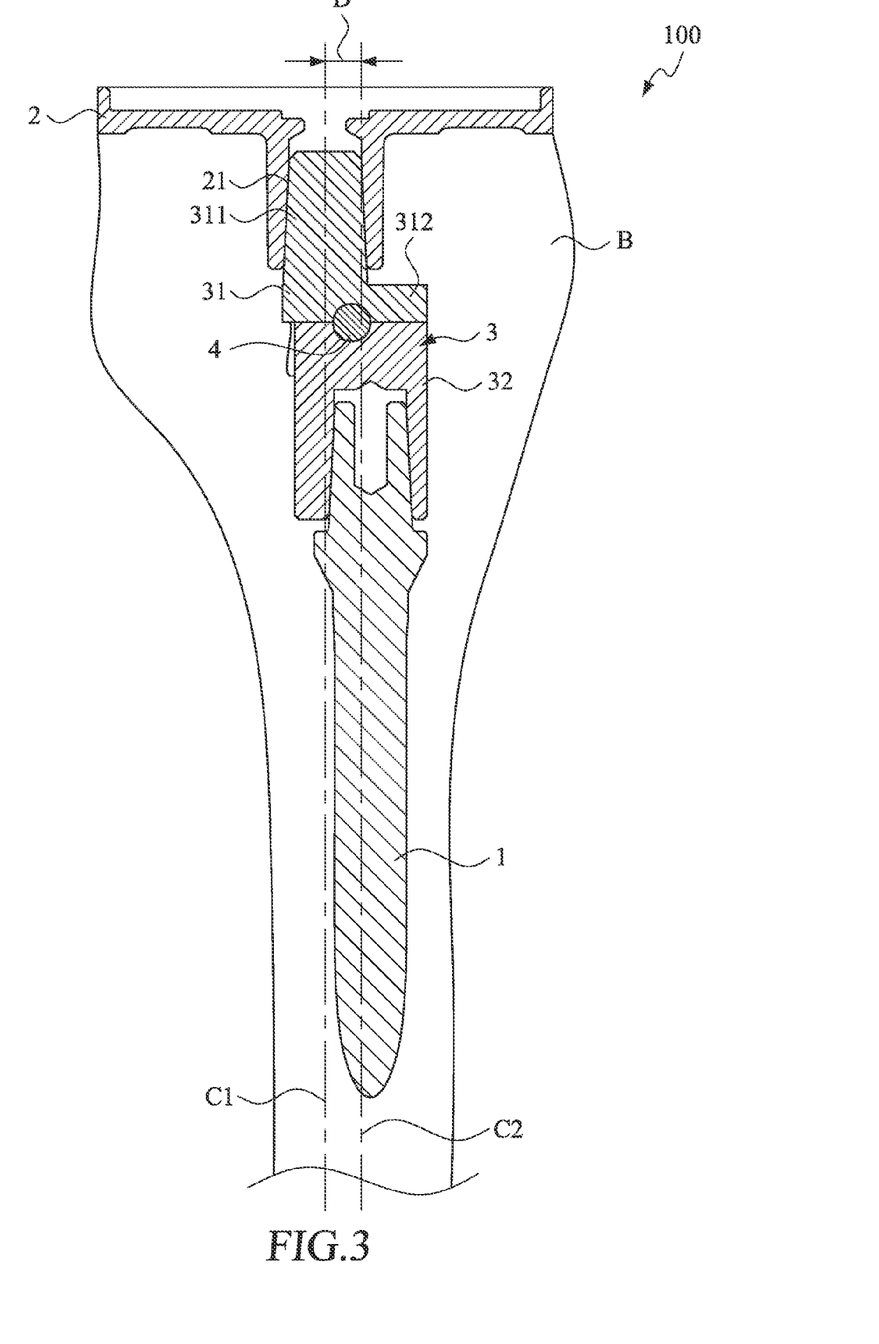
FIG. 3 is sectional view illustrating one application of the connecting device of joint prosthesis of the first embodiment according to the present invention.
Figure 10:
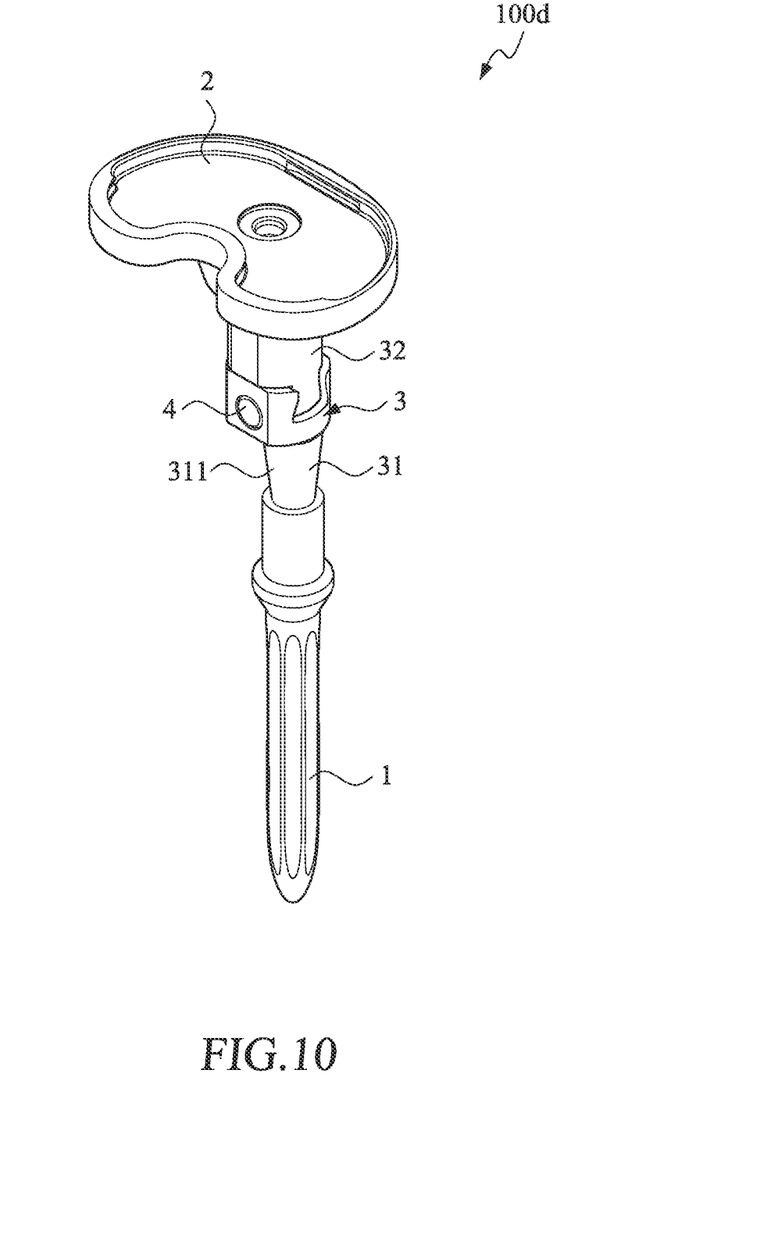
FIG. 10 is a stereogram illustrating the connecting device of joint prosthesis of the fifth embodiment according to the present invention.

The stem means 1 is provided for being inserted into a medullary cavity of a bone B (as shown in FIG. 3). The receiving means 2 is provided for receiving a bone structure (not shown) near the bone B, and the receiving means 2 has a receiving bore 21. For example, the stem means 1 is inserted into the medullary cavity of a tibia. And the receiving means 2 receives a bone structure near the tibia, such as part of the posterior stabilized knee, cruciate retaining knee, or hinged knee. Of course, in other embodiments, the stem means 1 may be inserted into the proximal femur, distal femur, or other bones. The stem means 1 and the receiving means 2 connect with each other by means of the offset connecting means 3. The offset connecting means 3 includes a first connecting component 31 and a second connecting component 32, wherein the first connecting component 31 and the second connecting component 32 connect with each other. In this embodiment, the first connecting component 31 connects with the receiving means 2 and the second connecting component 32 connects with the stem means 1 both in press riveting manner. Of course, the invention is not limited to that, the first connecting component 31 may connect with the stem means 1 and the second connecting component 32 may connect with the receiving means 2, as shown in FIG. 10. In addition, the first connecting component 31 and the second connecting component 32 may connect with the stem means 1 and the receiving means 2 respectively in other manners, such as screwing manner.

In this embodiment, the first connecting component 31 includes a column body 311 and a base body 312. The first connecting component 31 connects with receiving means 2 (or with the stem means 1, as shown in FIG. 10) by means of the column body 311. The first connecting component 31 has an engaging groove 313 for an engaging bump 323 of the second connecting component 32 to slide therein, so that the position of an inserting bore 314 of the first connecting component 31 can correspond to the position of an inserting recess 321 of the second connecting component 32. Of course, the engaging groove may be formed on the second connecting component and the engaging bump may be formed on the first connecting component so that the first connecting component can slide into the second connecting component. However, the present invention is not limited to that. In addition to the sliding manner, the first connecting component may connect with the second connecting component by means of other manners that can make the position of the inserting bore of the first connecting component correspond to the position of the inserting recess of the second connecting component. For example, the second connecting component may connect with the first connecting component by being inserted into the first connecting component along the longitudinal direction.

An inserting member 4 inserts into the inserting bore 314 of the first connecting component 31 and the inserting recess 321 of the second connecting component 32 to make the first connecting component 31 being fixed and positioned at the second connecting component 32. In this embodiment, the inserting member 4 is a pin and the inserting bore 314 is formed on a sidewall 315 of the first connecting component 31. The second connecting component 32 has two convex bodies 322 formed on an end facing the first connecting component 31 thereof, and the inserting recess 321 locates between the two convex bodies 322. Thereby, the inserting member 4 passes into the inserting bore 314 on the sidewall 315 and inserts into the inserting recess 321 in a direction orthogonal to a depth direction of the inserting recess 321 to make the first connecting component 31 being fixed and positioned at the second connecting component 32.

Figure 4:
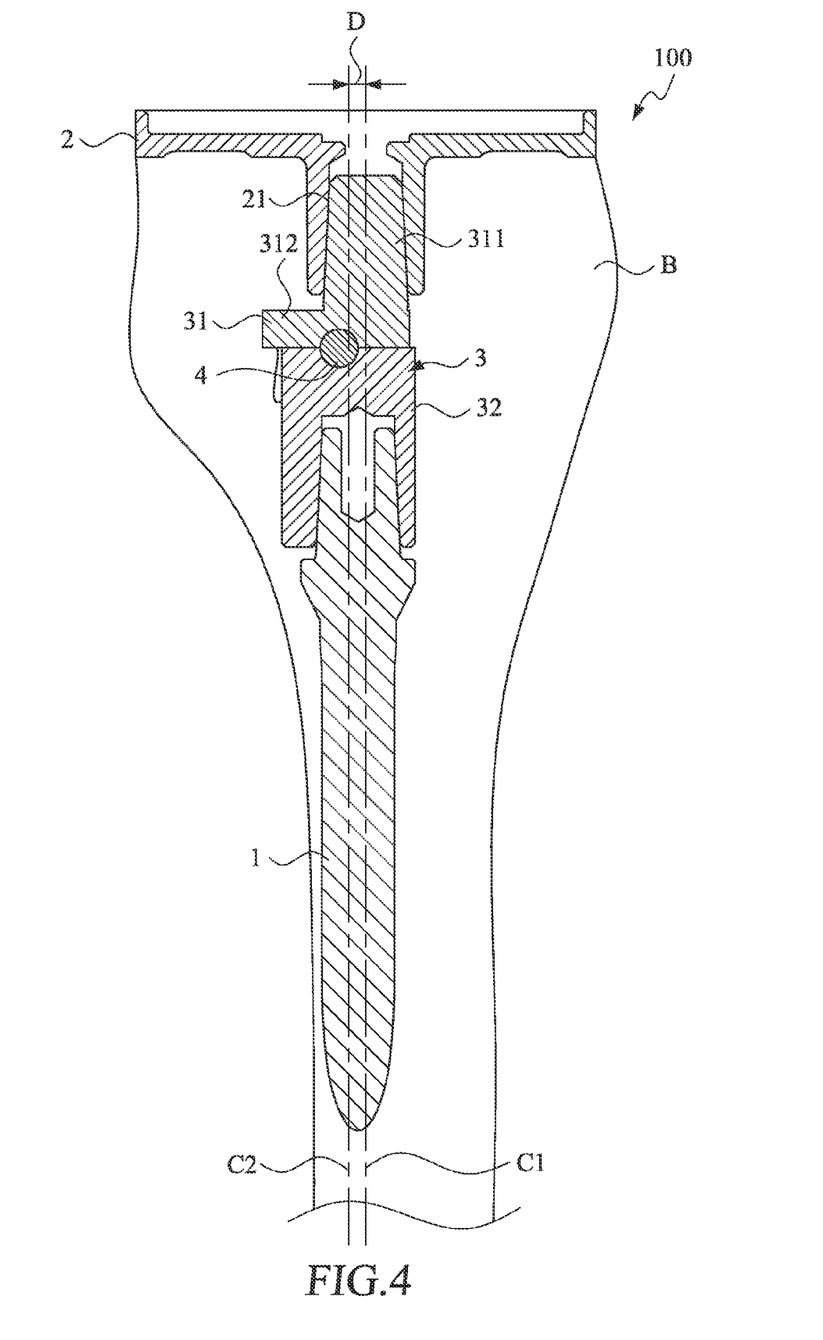
FIG. 4 is sectional view illustrating anther one application of the connecting device of joint prosthesis of the first embodiment according to the present invention.
Figure 9:
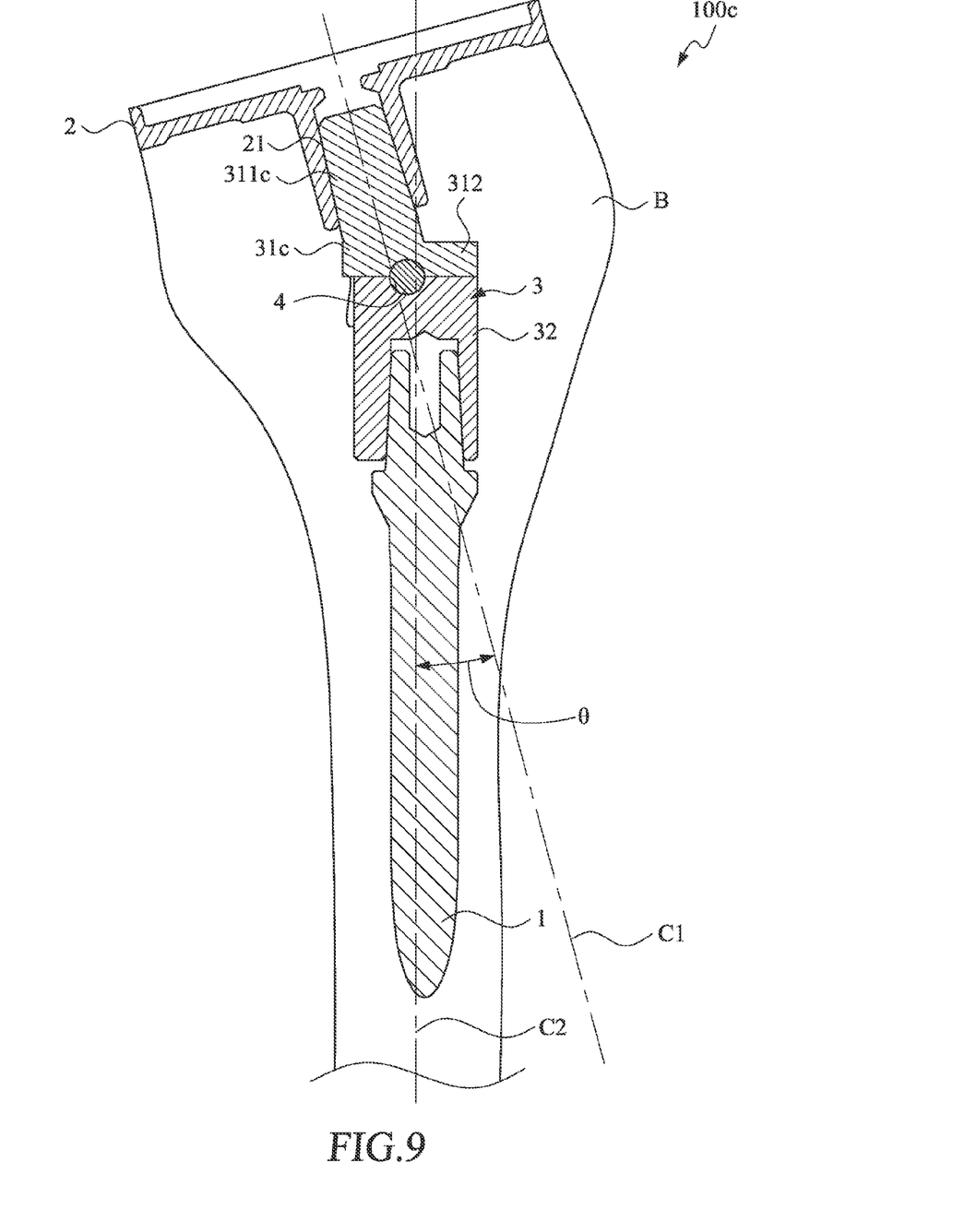
FIG. 9 is sectional view illustrating the application of the connecting device of joint prosthesis of the fourth embodiment according to the present invention.

When the first connecting component 31 is fixed and positioned at the second connecting component 32, there is an offset distance D between the longitudinal central axis C1 of the first connecting component 31 and the longitudinal central axis C2 of the second connecting component 32. Thus, there is also a relative offset distance between the longitudinal central axis of the stem means 1 and the longitudinal central axis of the receiving means 2, as shown in FIG. 3 and FIG. 4. The first connecting component 31 may be slided into the second connecting component 32 from both side of the second connecting component 32. And the column body 311 of the first connecting component 31 may be anterior to (as shown in FIG. 3) or posterior to (as shown in FIG. 4) the second connecting component 32, so that the stem means 1 connecting with the second connecting component 32 may be posterior to (as shown in FIG. 3) or anterior to (as shown in FIG. 4) the receiving means 2. Therefore, the connecting device 100 is adjustable to be suitable for individual patients regarding musculoskeletal mechanics. Of course, the stem means 1 may be selectively located in any orientations relative to the receiving means 2. In this embodiment, the longitudinal central axis C1 of the first connecting component 31 is parallel to the longitudinal central axis C2 of the second connecting component 32 (as shown in FIG. 3 and FIG. 4). However, the present invention is not limited to that. As shown in FIG. 9, the column body 311c is provided as being skew in relation to the base body 312, so that the longitudinal central axis of the first connecting component and the longitudinal central axis of the second connecting component are skew to each other. The longitudinal central axis C1 of the first connecting component 31c may intersect with the longitudinal central axis C2 of the second connecting component 32 to form an included angle θ therebetween, wherein the included angle θ may be any degree. Alternately, the longitudinal central axis of the first connecting component may not intersect with and be skew to the longitudinal central axis of the second connecting component. Moreover, the quantity of the first connecting component and the second connecting component is not limited to be in a number of one. The stem means 1 and the receiving means 2 may connect with each other by having a plurality of first connecting components and a plurality of second connecting components connected therebetween so that a plurality of offset distances D are formed for being adjusted.

Figure 5:
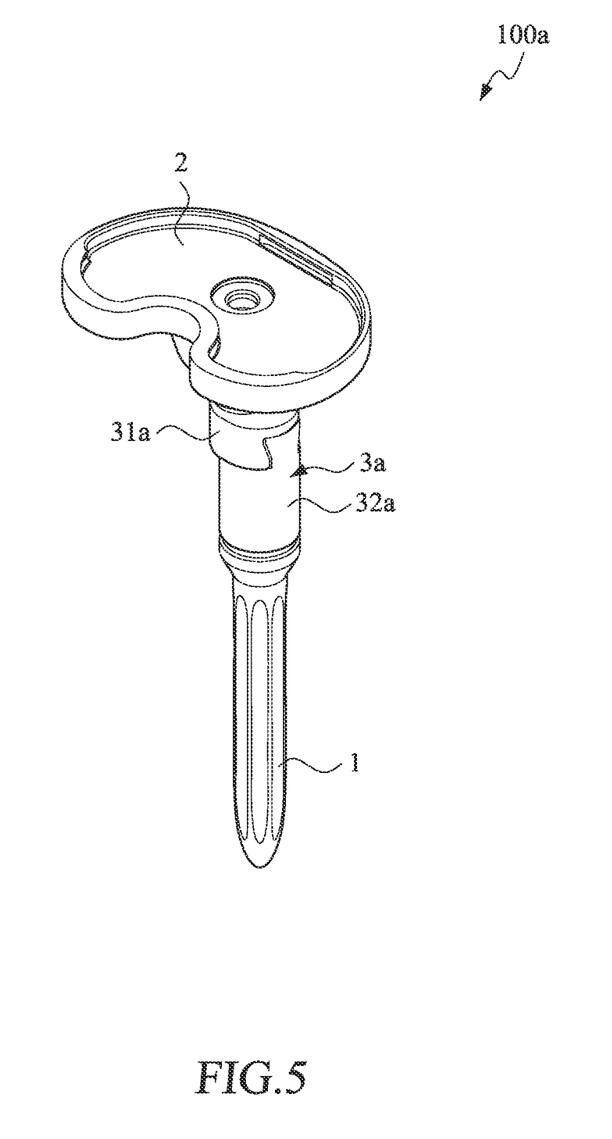
FIG. 5 is a stereogram illustrating the connecting device of joint prosthesis of the second embodiment according to the present invention.
Figure 6:
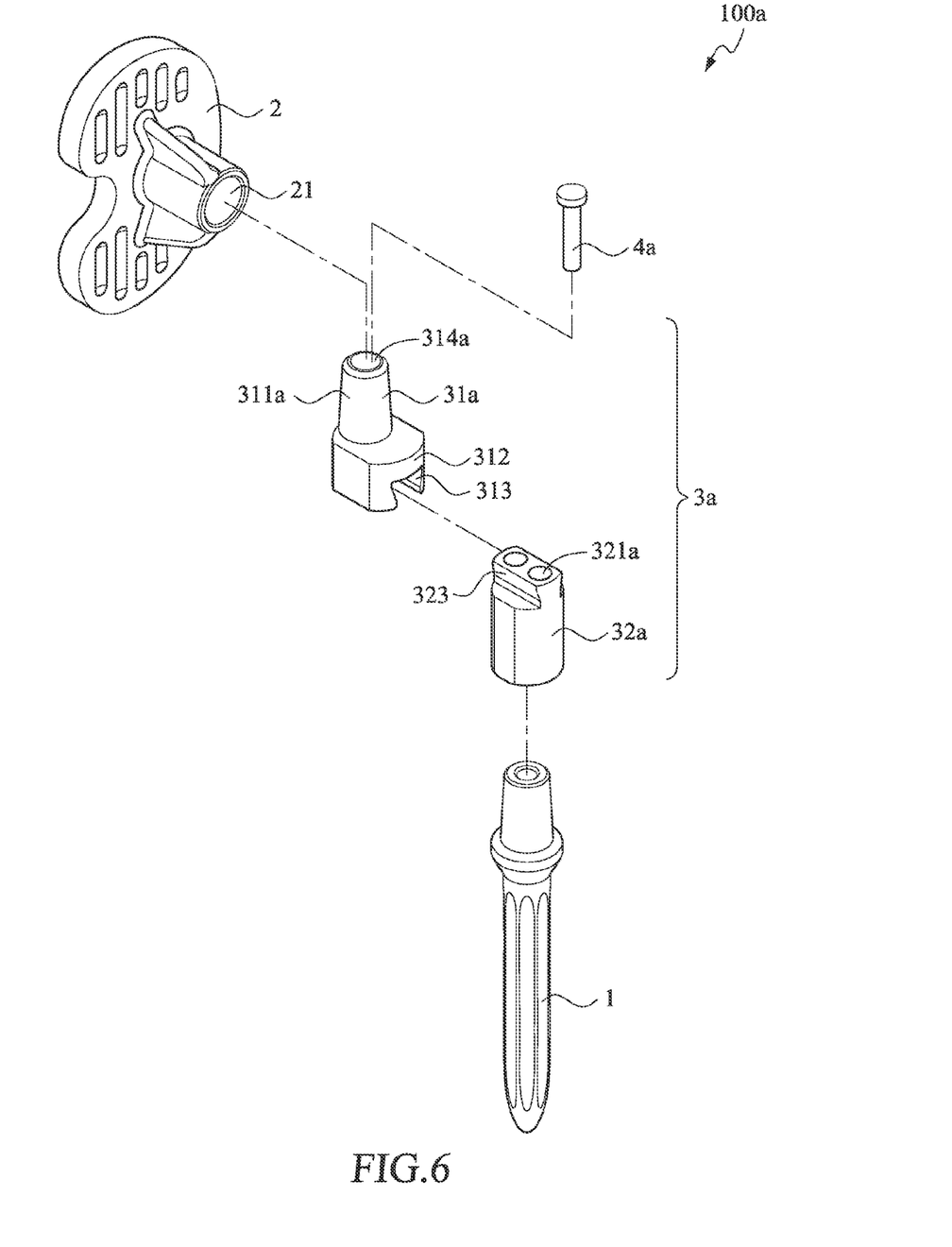
FIG. 6 is an explosion diagram illustrating the connecting device of joint prosthesis of the second embodiment according to the present invention.

Refer to FIG. 5 and FIG. 6. FIG. 5 is a stereogram illustrating the connecting device of joint prosthesis of the second embodiment according to the present invention. FIG. 6 is an explosion diagram illustrating the connecting device of joint prosthesis of the second embodiment according to the present invention. The elements of this embodiment illustrated in these two Figs. are similar to those in the first embodiment. The connecting device 100*a* of the second embodiment is different from the connecting device 100 of the first embodiment in follows. In this embodiment, an inserting bore 314*a* of the first connecting component 31*a* of the connecting device 100*a* penetrates the column body 311*a*. The second connecting component 32*a* of the connecting device 100*a* has a plurality of inserting recesses 321*a* on a side facing the first connecting component 31*a* thereof. In this embodiment, the inserting member 4*a* is a pin. By inserting the inserting member 4*a* into the inserting bore 314*a* and one inserting recess 321*a* selected from a plurality of inserting recesses 321*a* through the column body 311*a*, the first connecting component 31*a* is fixed and positioned at the second connecting component 32*a*. In other embodiments, the inserting member 4*a* may be a screw member.

Figure 7:
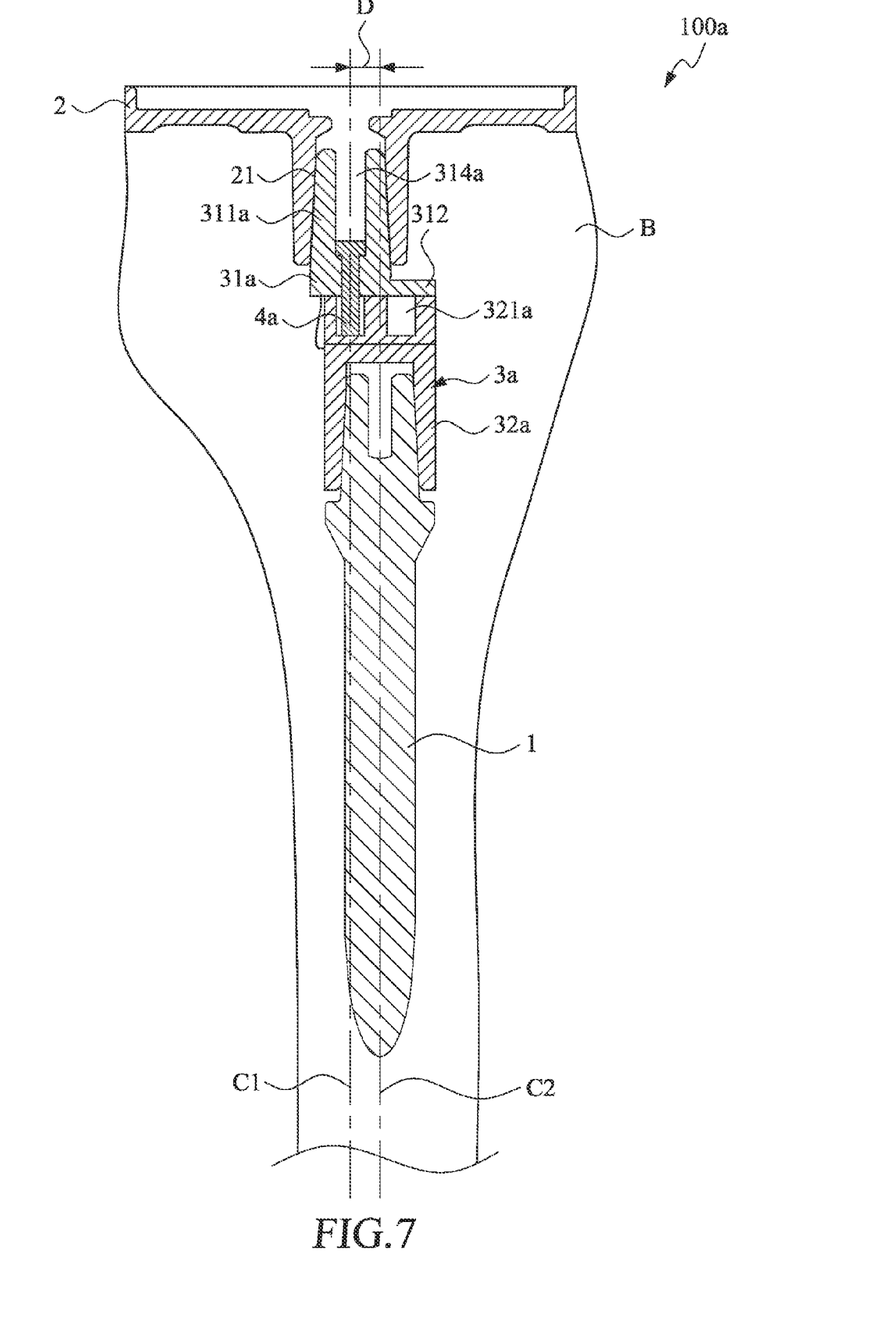
FIG. 7 is sectional view illustrating the application of the connecting device of joint prosthesis of the second embodiment according to the present invention.

Similarly, when the first connecting component 31*a* is fixed and positioned at the second connecting component 32*a*, there is an offset distance D between the longitudinal central axis C1 of the first connecting component 31*a* and the longitudinal central axis C2 of the second connecting component 32*a*, as shown in FIG. 7. And similarly, the stem means 1 may selectively be anterior to, posterior to, lateral to, or medial to the receiving means 2. Furthermore, the length of the offset distance D can be adjusted by inserting the inserting member 4*a* into certain one inserting recess 321*a* selected from a plurality of the inserting recesses 321*a*. In other words, the variety and the adjustment accuracy of the length of the offset distance D can be raised by increasing the quantity of the inserting recess 321*a* so as to make the connecting device fit individual patients with more effect in regard of the musculoskeletal mechanics.

Figure 8:
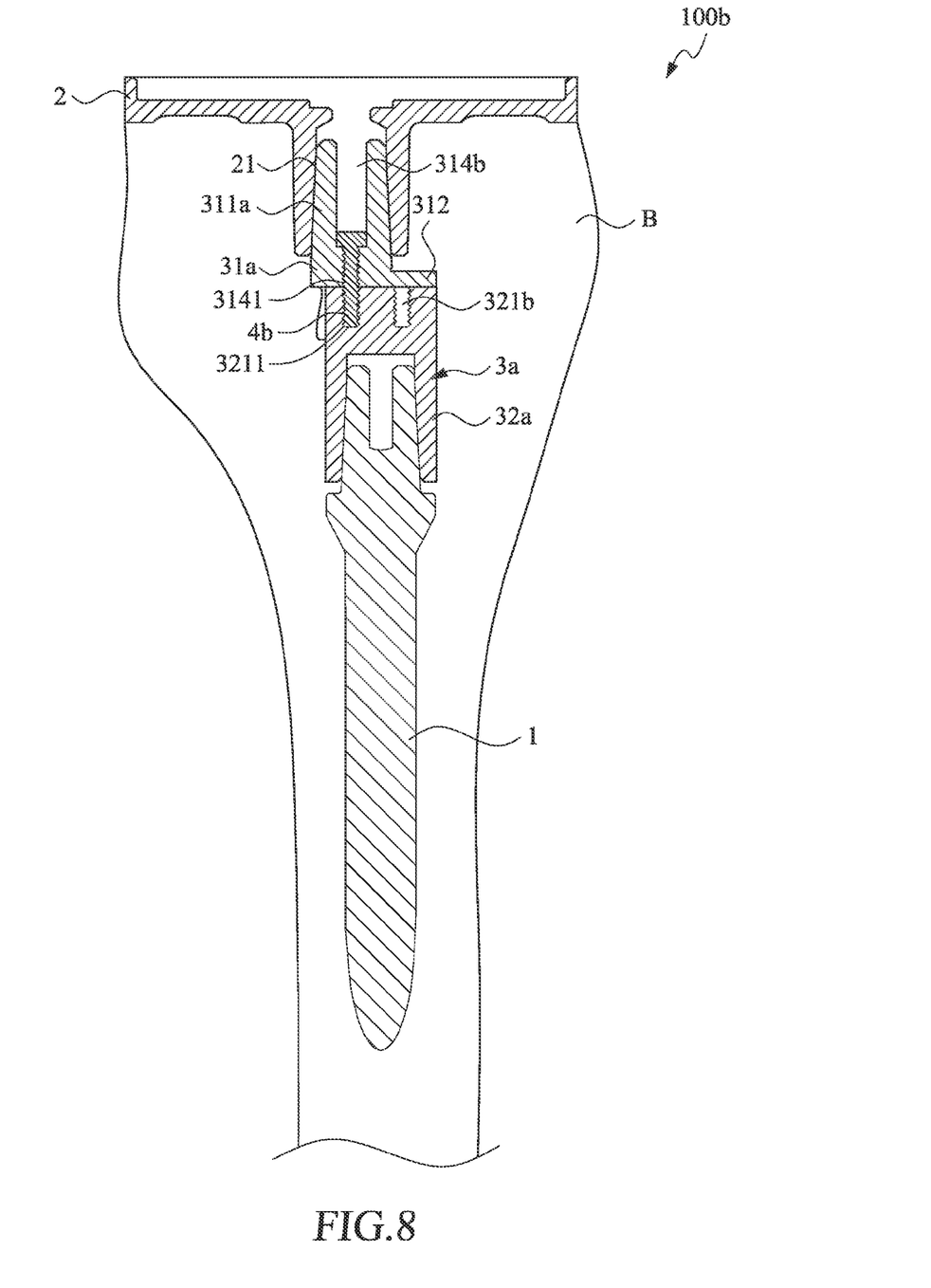
FIG. 8 is sectional view illustrating the application of the connecting device of joint prosthesis of the third embodiment according to the present invention.

As show in FIG. 8, in a preferred embodiment, the inserting member 4*b* is a screw member. The inserting recess 321*b* has an inner screw section 3211. For example, the inner screw section 3211 may be a screw member formed on the inner wall surface of the inserting recess 321*b*. Also, the inner wall surface of the inserting bore 314*b* may have a screw member 3141. The inserting member 4*b* is fixed by both of the screw member 3141 and the inner screw section 3211 so that is inserted into the inserting bore 314*b* and the inserting recess 321*b* more tightly.

Overall, it can be known that the connecting device of the present invention is not only adjustable in view of position and offset direction for fitting individual patients, but also easy and convenient to be assembled and adjusted.

The above description should be considered as only the discussion of the preferred embodiments of the present invention. However, a person skilled in the art may make various modifications to the present invention. Those modifications still fall within the spirit and scope defined by the appended claims.

What is claimed is:

1. A connecting device of joint prosthesis, comprising:
a stem means for being inserted into a medullary cavity of a bone;
a receiving means for receiving a bone structure near the bone, the receiving means having a receiving bore;
an offset connecting means connected between the stem means and the receiving means, the offset connecting means including a first connecting component and a second connecting component, the first connecting component having an inserting bore and a column body that extends toward the receiving means and is received by the receiving bore, the second connecting component having an inserting recess and an engaging bump, and the engaging bump extending from left upper side to right upper side on an side surface facing toward the receiving means, wherein the column body is provided on a side facing toward the receiving means in a position with an offset distance from the middle of the side facing toward the receiving means, and the engaging bump is slide within an engaging groove of the first connecting component either from the left upper side of the engaging bump or from the right upper side of the engaging bump; and
an inserting member inserting into the inserting bore and the inserting recess to make the first connecting component being fixed and positioned at the second connecting component,
wherein when the inserting member passes through the inserting bore to insert into the inserting recess in a direction perpendicular to the extending direction of the column body, the inserting recess is extended in a direction parallel to the insertion direction of the inserting member,
wherein when the inserting member passes through the inserting bore to insert into the inserting recess in a direction parallel to the extending direction of the column body, the inserting recess is a plural inserting holes that are extended in a direction parallel to the insertion direction of the inserting member.

2. The connecting device of joint prosthesis as claimed in claim 1, wherein the inserting member is a screw member or a pin.

3. The connecting device of joint prosthesis as claimed in claim 1, wherein the inserting bore penetrates the column body.

4. The connecting device of joint prosthesis as claimed in claim 1, wherein the inserting recess has an inner screw section, the inserting member passes into the inserting bore and is fixed by the inner screw section.

5. The connecting device of joint prosthesis as claimed in claim 1, wherein the second connecting component has a plurality of the inserting recesses.

6. The connecting device of joint prosthesis as claimed in claim 1, wherein the second connecting component has two convex bodies formed on an end facing the first connecting component thereof, the inserting recess locates between the two convex bodies, and the inserting member inserts into the inserting recess in a direction orthogonal to a depth direction of the inserting recess.

7. The connecting device of joint prosthesis as claimed in claim 1, wherein the inserting bore is formed on a sidewall of the first connecting component.

8. The connecting device of joint prosthesis as claimed in claim 1, wherein the longitudinal central axis of the first connecting component and the longitudinal central axis of the second connecting component are skew to each other.

* * * * *